US009675518B2

(12) United States Patent
Thoresen et al.

(10) Patent No.: US 9,675,518 B2
(45) Date of Patent: Jun. 13, 2017

(54) NON-INVASIVE METHODS FOR PREVENTION, DETECTION, TREATMENT, AND HEALING OF NEOPLASTIC PROCESSES IN HUMANS

(71) Applicant: GOOD-IP LIMITED, Nicosia (CY)

(72) Inventors: Are Thoresen, Sandefjord (NO); Michael Schlosser, Haifa (IL)

(73) Assignee: Good-IP Limited, Nicosia (CY)

(*) Notice: Subject to any disclaimer, the term of this patent is extended or adjusted under 35 U.S.C. 154(b) by 302 days.

(21) Appl. No.: 14/159,481

(22) Filed: Jan. 21, 2014

(65) Prior Publication Data

US 2015/0202118 A1 Jul. 23, 2015

(51) Int. Cl.
*A61B 19/00* (2006.01)
*A61H 39/08* (2006.01)
(Continued)

(52) U.S. Cl.
CPC ......... *A61H 39/086* (2013.01); *A61B 5/4854* (2013.01); *A61H 39/002* (2013.01);
(Continued)

(58) Field of Classification Search
CPC .................. A61H 39/00; A61H 39/002; A61H 2039/005; A61H 39/007; A61H 39/02;
(Continued)

(56) References Cited

U.S. PATENT DOCUMENTS 4,232,678 A * 11/1980 Skovajsa .............. A61N 5/0619 128/907
5,250,068 A * 10/1993 Ideguchi ................ A61B 18/22 128/907
(Continued)

FOREIGN PATENT DOCUMENTS

| | | |
|---|---|---|
| CN | 2254347 Y | 5/1997 |
| CN | 101982161 A | 3/2011 |

(Continued)

OTHER PUBLICATIONS

Are Simeon Thoresen DVM, "Holistic Veterinary Medicine", CreateSpace Independent Publishing Platform, North Charleston, South Carolina, USA 2nd Ed.,466-484 (2012).
(Continued)

*Primary Examiner* — Ahmed Farah
(74) *Attorney, Agent, or Firm* — Roach Brown McCarthy & Gruber P.C.; Kevin D. McCarthy

(57) ABSTRACT

The invention is a method consisting of stimulation of specific new acupuncture points to prevent, detect, treat and heal specific types of neoplastic process in humans. The specific acupuncture points used in the method of the invention have not been previously disclosed for the treatment of neoplastic processes. The treatments can be carried out by accredited practitioners in a clinical setting or by the patient her/himself at home. The stimulation can be provided by any of the known techniques used for stimulation of controlling points, including, but not limited to, traditional acupuncture needles, auto-injector needles, electric acupuncture, acupressure, lasers, acupuncture lasers, UV radiation, infra-red radiation, heat, magnets, moxibustion, and a combination of two or more of these techniques, for example, the use of both needles and laser acupuncture simultaneously in a single treatment session. The method of the invention is also used for detection and prevention of neoplastic process.

16 Claims, 5 Drawing Sheets

(51) Int. Cl.

| | |
|---|---|
| ***A61H 39/00*** | (2006.01) |
| ***A61H 39/04*** | (2006.01) |
| ***A61H 39/06*** | (2006.01) |
| ***A61B 5/00*** | (2006.01) |
| ***A61M 5/42*** | (2006.01) |
| ***A61M 5/52*** | (2006.01) |
| ***A61N 2/00*** | (2006.01) |
| ***A61N 5/06*** | (2006.01) |
| *A61N 2/06* | (2006.01) |
| *A61N 5/067* | (2006.01) |

(52) U.S. Cl.

CPC ............. *A61H 39/04* (2013.01); *A61H 39/06* (2013.01); *A61M 5/427* (2013.01); *A61M 5/52* (2013.01); *A61N 2/006* (2013.01); *A61N 5/0619* (2013.01); *A61H 2039/005* (2013.01); *A61H 2201/0119* (2013.01); *A61H 2201/10* (2013.01); *A61H 2201/164* (2013.01); *A61H 2201/1635* (2013.01); *A61H 2201/1666* (2013.01); *A61H 2201/1671* (2013.01); *A61H 2205/065* (2013.01); *A61H 2205/12* (2013.01); *A61N 2/06* (2013.01); *A61N 2005/067* (2013.01)

(58) Field of Classification Search

CPC ...... A61H 39/04; A61H 39/08; A61H 39/083; A61H 39/086; A61N 1/36; A61N 1/3605; A61N 1/36057; A61N 1/3606; A61N 5/0622; A61N 5/067

USPC .... 607/1–3, 46, 48, 88, 89, 96, 98, 99, 108, 607/111, 115–118; 128/898, 907; 600/548

See application file for complete search history.

(56) References Cited

U.S. PATENT DOCUMENTS

| | | | | |
|---|---|---|---|---|
| 5,409,482 | A * | 4/1995 | Diamantopoulos | A61N 5/06 606/10 |
| 6,306,160 | B1 | 10/2001 | Nidetzky | |
| 7,179,278 | B2 | 2/2007 | Schikora | |
| 7,904,173 | B2 * | 3/2011 | Kim | A61N 1/40 607/115 |
| 8,343,026 | B2 * | 1/2013 | Gardiner | A61B 5/4824 600/9 |
| 8,932,198 | B1 * | 1/2015 | You | A61B 17/545 600/27 |
| 2005/0154317 | A1 | 7/2005 | Shin | |
| 2007/0129713 | A1 | 6/2007 | Weber | |
| 2011/0150924 | A1 * | 6/2011 | Della Rocca | A61K 39/39 424/204.1 |
| 2012/0158042 | A1 | 6/2012 | Cho | |
| 2013/0023722 | A1 * | 1/2013 | Kruk | A61M 5/14244 600/27 |
| 2013/0079582 | A1 | 3/2013 | Della Rocca | |
| 2013/0172969 | A1 * | 7/2013 | You | A61F 7/034 607/114 |
| 2016/0008221 | A1 * | 1/2016 | Greiner | A61H 39/002 607/72 |

FOREIGN PATENT DOCUMENTS

| | | | |
|---|---|---|---|
| CN | 102716553 | A | 10/2012 |
| CN | 202526546 | A | 11/2012 |
| WO | 2009/142993 | A1 | 11/2009 |

OTHER PUBLICATIONS

National Cancer Institute: PDQ® Acupuncture. Bethesda, MD: National Cancer Institute. Date last modified <Apr. 16, 2013>. Available at: http://www.cancer.gov/cancertopics/pdq/cam/acupuncture/healthprofessional. Accessed <May 10, 2013>).

"Acupuncture: Review and Analysis of Reports on Controlled Clinical Trials" (http://apps.who.int/medicinedocs/en/d/Js4926e/5.html)—last modified on Apr. 16, 2013.

International Search Report for PCT/IL15/50065, mailed Jun. 9, 2015, 3 pages.

* cited by examiner

NON-INVASIVE METHODS FOR PREVENTION, DETECTION, TREATMENT, AND HEALING OF NEOPLASTIC PROCESSES IN HUMANS

FIELD OF THE INVENTION

The invention is from the field of integrative medicine. Specifically the invention is from the field of stimulation of acupoints. More specifically the invention is from the field of acupuncture therapy and the stimulation of acupoints applied to the prevention, detection, and treatment of a variety of types of abnormal tissue growth in humans.

BACKGROUND OF THE INVENTION

Acupuncture is one or of the oldest methods of treating disease having been used by the Chinese for over 4000 years. Without going into the philosophy behind it, the traditional Chinese method (TCM) is based on stimulating specific points on the body known as acupuncture points by penetrating the skin with thin sharp needles and manipulating the needles. The acupuncture points are located on paths called meridians through which energy flows throughout the body. Also a long standing aspect of TCM is a therapy called moxibustion, which involves burning a herb either directly on the patient's skin at an acupuncture point or in association with a needle.

Over the millennia that have passed since the origins of the practice of acupuncture new systems have evolved that use acupuncture points and meridians not recognized in the traditional Chinese method (TCM). Additionally new methods of applying the therapy that are non-invasive and do not require the use of needles have been devised. These methods include, for example, electric acupuncture, acupressure, and laser acupuncture.

Soft Lasers—low-intensity non-thermal laser irradiation treatments are used to stimulate traditional acupuncture points instead of needles; in other cases they are used to stimulate the traditional acupuncture points by applying the technique of moxibustion. Many different apparatuses have been described in the patent and non-patent literature for use in laser acupuncture. Some examples are:

U.S. Pat. No. 6,306,160 describes a hand held device that comprises an electrode used to locate acupuncture points by measuring skin resistance and a 3 mw diode laser that emits light with a wavelength of 635-670 nm.

U.S. Pat. No. 7,179,278 describes an apparatus in which one or more remote laser sources that emit light at 350-980 nm are optically linked by fiber optics to a handpiece that is in contact with the skin of the patient. The handpiece comprises two electrodes to measure skin resistance. The penetration depth is adjusted by changing the wavelength and also by reducing the diameter of the optical fiber as it approaches the tip of the handpiece.

US 2007/0129713 describes a laser needle for performing combined laser therapy and electric therapy. The output beam from a remote diode laser is conducted to the patient by an optical fiber. At its distal end the optical fiber is surrounded by a metal jacket having a disk attached to its lower end. The disk serves to distribute the electric current of the electric acupuncture over a larger area and also to aid in attaching the laser needle to the body of the patient.

CN102716553 is an example of a publication that describes an apparatus comprising two lasers that provides the combined effects of needle and moxibustion. The first laser is a red laser (635 nm) to simulate the effect of the needles and the second laser produces an output in the range of 1250-10000 nm to simulate the effect of thermal moxibustion.

Acupuncture treatments are generally carried out by highly trained and experienced practitioners; however, guides for helping non-experienced persons to administer acupuncture treatments have been suggested. Examples of these guides are CN101982161A, which describes shirts on the outer surface of which have been marked acupuncture channels and points. CN202526546U describes articles of clothing adapted for acupuncture or moxibustion therapy by providing holes through the material at the location of acupoints. CN2254347Y describes acupuncture massage clothes that respectively have plastic needles on the inside of the clothing located at acupoints.

Although there are innumerable reports of successful treatment of essentially every known condition relating to the physical and mental health of humans and animals, a considerable amount of controversy surrounding the efficacy of the method exists. This is in a large part due to the difficulty of devising and carrying out controlled clinical studies.

In an effort to make some order out of the conflicting reports, the World Health Organization published in 2004 a report entitled "Acupuncture: Review and Analysis of Reports on Controlled Clinical Trials" (http://apps.who.int/medicinedocs/en/d/Js4926e/5.html). This report is somewhat outdated since it only includes the results of controlled clinical trials that were formally published through the year 1998; nonetheless the report contains a comprehensive list of diseases and disorders that can be treated with acupuncture. The diseases or disorders for which acupuncture therapy has been tested in controlled clinical trials reported in the recent literature are classified into the following four categories:

1. Twenty-three diseases, symptoms or conditions for which acupuncture has been proved—through controlled trials—to be an effective treatment. The only item in the list that is related to treatment of cancer is adverse reactions to radiotherapy and/or chemotherapy.
2. Sixty-three diseases, symptoms or conditions for which the therapeutic effect of acupuncture has been shown but for which further proof is needed. The only item in the list that is related to treatment of cancer is cancer pain.
3. Eight diseases, symptoms or conditions for which there are only individual controlled trials reporting some therapeutic effects, but for which acupuncture is worth trying because treatment by conventional and other therapies is difficult. This list contains no items related to treatment of cancer.
4. Six diseases, symptoms or conditions for which acupuncture may be tried provided the practitioner has special modern medical knowledge and adequate monitoring equipment. This list contains no items related to treatment of cancer.

The American National Cancer Institute associated with the National Institutes of Health has issued a report on the recognized use of acupuncture in treatment of cancer. The study appears in a short version intended for patients (http://www.cancer.gov/cancertopics/pdq/cam/acupuncture/patient/)

and a much more detailed version intended for health care professionals (National Cancer Institute: PDQ® Acupuncture. Bethesda, Md.: National Cancer Institute. Date last modified <April/16/2013>. Available at: http://www.cancer.gov/cancertopics/pdq/cam/acupuncture/healthprofessional. Accessed <May/10/2013>). The later document contains a comprehensive report of laboratory/animal preclinical and human clinical studies of cancer related symptoms and is regularly updated. The summary from NCI's PDQ cancer information summary states the following:

"It is noteworthy that almost all reported clinical studies on the effects of acupuncture on cancer or cancer therapy-related symptoms focus on symptom management rather than the disease itself. Investigations into the effects of acupuncture on chemotherapy-induced nausea and vomiting; many of which were randomized and well-controlled produced the most convincing findings. Although a considerable number of favorable clinical acupuncture studies have been reported, most were case studies, clinical observations, or nonrandomized and poorly controlled clinical trials. In many studies, methodologic flaws in clinical study design hampered rigorous scientific efforts to evaluate the effects o/acupuncture. Although pain relief is the most clinically common use of acupuncture, only a few studies on cancer pain are well-controlled or have sample sizes large enough to support their findings."

This summary agrees with the earlier WHO study and shows that at this moment in time the view of the conventional medical establishment including the regulating authorities in most countries is that the place of acupuncture in cancer therapy is to alleviate pain and anxiety, which are often the side-effects of the surgery and chemo and radiation therapies that conventional cancer treatment employs.

Despite the lack of official recognition of the effectiveness of acupuncture in treating cancerous growths many practitioners have been and are actively engaged in developing acupuncture methodologies for treating cancer. These practitioners believe that if their methods are employed to correct the root cause of the disease, then there will be no need to deal with the symptoms described above. The assistance of these practitioners is often actively sought out by cancer patients and not infrequently physicians recommend acupuncture, in their view as a last resort, to patients that cannot be helped by conventional methods.

Are Thoresen, one of the inventors (henceforth "the first inventor") of the present invention, has been actively practicing acupuncture therapy since 1977. He has treated more than 600 patients—animals and humans—with various kinds of cancer, applying different methods. Some of the experience that he has accumulated over the years is summarized in a book that he has written in his native Norwegian. A $2^{nd}$ English edition has been published (Are Simeon Thoresen DVM, "Holistic Veterinary Medicine", CreateSpace Independent Publishing Platform, North Charleston, S.C., USA).

It is a purpose of the present invention to build on the first inventor's experience and his previous success by providing a system and method that is based upon the use of acupuncture points that have not previously been reported for prevention, detection, and treatment of cancer.

Further purposes and advantages of this invention will appear as the description proceeds.

SUMMARY OF THE INVENTION

In a first aspect the invention is a method for treating, by stimulation of specific acupoints, neoplastic processes that have previously been diagnosed in specific organs in human patients who are or are not currently undergoing other treatment, the method comprising the steps of:

a) the patient, visits her/his attending medical specialist or an accredited acupuncture practitioner who decides which of the specific acupoints should be stimulated and prepares a therapy protocol;

b) the patient undergoes a series of treatment sessions comprised of stimulation of the specific acupoints, which are located on his/her hands and feet, wherein the stimulation can be provided by at least one of any stimulation means used to apply acupuncture therapy;

c) the patient periodically visits her/his attending medical specialist who uses known methods to evaluate the effect of the treatment on the neoplastic process;

d) according to the evaluation of the progress, the attending medical specialist or the accredited acupuncture practitioner adjusts the treatment protocol;

e) steps (c) to (d) are repeated until the treatment is deemed successful.

In embodiments of the method of the first aspect of the invention:

i) in step (a) said patient consults instructional material available to her/him and decides which of the specific acupoints should be stimulated and prepares a therapy protocol accordingly, without the assistance of her/his attending medical specialist or an accredited acupuncture practitioner;

ii) in step (b) the treatment sessions are carried out by the patient or a family member or another layperson in the patient's home;

iii) in step (d) the patient her/himself adjusts the treatment protocol with or without the help of her/his attending medical specialist or an accredited acupuncture practitioner.

In embodiments of the method of the first aspect of the invention the at least one stimulation means is selected from the group including but not limited to: traditional acupuncture needles, auto-injector needles, electric acupuncture apparatus, acupressure devices, lasers, UV radiation sources, infra-red radiation sources, heat sources, magnets, fire, and a combination of at least two of these means.

In embodiments of the method of the invention the treatment sessions are initially carried out once a week for at least 3 months.

In embodiments of the method of the invention each treatment session comprises one of the following: using low-level laser radiation alone for 8-10 minutes for each relevant acupoint; using acupuncture needles alone for 20 minutes per acupoint; and using a combined treatment with acupuncture needles and low-level laser radiation comprised of using the acupuncture needles alone for 12 minutes followed by use of the low-level laser and the acupuncture needles together for 8 minutes.

According to the method of the invention, for human patients, the location of the acupuncture points on the feet and hands of the patients that are relevant for treatment of cancer occurring in specific organs are the acupoints numbered 1 to 13 shown in FIG. 1 and acupoints numbered 1 to 9 in FIG. 2 respectively. The acupoints numbered 1-13 in FIG. 1 will also be referred to herein as A1 to A13 respectively and the acupoints numbered 1-9 in FIG. 2 will also be referred to herein as B1 to B9 respectively; wherein:

a) in FIG. 1: acupoint 1=Kidney; acupoint 2=Bladder; acupoint 3=Breast; acupoint 4=Stomach; acupoint 5=Pancreas; acupoint 6=Prostata & Uterus; acupoint 7=Thyroid; acupoint 8=Small Intestine; acupoint 9=Uterus; acupoint 10=Ovary; acupoint 11=Prostate; acupoint 12=Large Intestine; and acupoint 13=Rectum & Anus; and b) in FIG. 2: acupoint 1=Liver; acupoint 2=Testis; acupoint 3=Cervix; acupoint 4=Prostata & Uterus; acupoint 5=Lungs; acupoint 6=Kidney; acupoint 7=Bladder; acupoint 8=Large Intestine; and acupoint 9=Rectum & Anus.

According to the method of the invention, for human patients, a neoplastic process occurring in one of the following specific organs is treated by stimulating at least one acupuncture point associated with the organ, the associated acupoints located at the following locations:

i. anus—A13=14/20 on the medial side of 5th metatarsal and B9=14/20 on the medial side of 5th metacarpal;
ii. bladder—A2=11/20 on the medial side of 1st metatarsal and B7=11/20 on the medial side of 5th metacarpal;
iii. breast—A3=6/20 on the lateral side of 1st metatarsal;
iv. cervix—B3=between the distal ⅔ and the proximal ⅓ on the lateral side of the proximal digital bone of the 4th digit;
v. kidney—A1=10/20 on the medial side of 1st metatarsal and B6=10/20 on the medial side of 5th metacarpal;
vi. large intestine—A12=12/20 on the medial side of 5th metatarsal and B8=12/20 on the medial side of 5th metacarpal;
vii. liver—B1=10/20 on the medial side of 1st metacarpal;
viii. lungs—B5=6/20 on the medial side of 5th metacarpal;
ix. ovary—A10=10/20 on the medial side of 5th metatarsal;
x. pancreas—A5=9/20 on the lateral side of 1st metatarsal;
xi. prostata—A6=10/20 on the lateral side of 1st metatarsal and 11/20 on the medial side of 5th metatarsal and B4=11/20 on the lateral side of 4th metacarpal;
xii. rectum—A13=14/20 on the medial side of 5th metatarsal and B9=14/20 on the medial side of 5th metacarpal;
xiii. small intestine—A8=8/20 on the medial side of 5th metatarsal;
xiv. stomach—A4=8/20 on the lateral side of 1st metatarsal;
xv. testis—B2=11/20 on the medial side of 1st metacarpal;
xvi. thyroid—A7=4/20 on the medial side of 5th metatarsal; and
xvii. uterus—A6=10/20 on the lateral side of 1st metatarsal and B4=10/20 on the medial side of 5th metatarsal and 11/20 on the lateral side of 4th metacarpal;

wherein, the locations are expressed as the lengths of the bones, which are divided into twenty parts starting from the distal end and each of the acupoints is located within the indicated 20th part of the bone.

In embodiments of the method of the first aspect of the invention the corresponding points on both hands or on both feet are stimulated either simultaneously or consecutively.

In embodiments of the method of the first aspect of the invention after the treatment is deemed successful, treatment sessions are carried out periodically for the remainder of the patient's life.

In a second aspect the invention is a method for the diagnoses of the probability of the presence of or probability of development of neoplastic processes in a human patient. The diagnostic method comprising:

a. carrying out a diagnostic session comprised of successively stimulating at least one of the acupoints referred to as A1 to A13 and B1 to B9; and
b. determining the probability based on feedback received from the patient In embodiments of the second aspect of the invention the diagnostic session comprises one of the following: using low-level laser radiation alone for 8-10 minutes for one, or some, or each relevant acupoint; using acupuncture needles alone for 20 minutes per acupoint; and using a combined treatment with acupuncture needles and low-level laser radiation comprised of using the acupuncture needles alone for 12 minutes followed by use of the low-level laser and the acupuncture needles together for 8 minutes.

In embodiments of the second aspect of the invention the diagnostic sessions are carried out once every three months.

In a third aspect the invention is a method for preventing the occurrence of a specific type of neoplastic process in any given patient, including a patient having a family history or genetic makeup that increases his/her risk of contracting the specific type of neoplastic process. The preventive method comprising periodically carrying out a preventive treatment session comprised of stimulation of the specific acupuncture points selected from the acupoints referred to as A1 to A13 and B1 to B9 listed herein above that are relative to the specific type of neoplastic process one wishes to prevent.

In embodiments of the third aspect of the invention each preventive treatment session comprises one of the following: using low-level laser radiation alone for 8-10 minutes for each relevant acupoint; using acupuncture needles alone for 20 minutes per acupoint; and using a combined treatment with acupuncture needles and low-level laser radiation comprised of using the acupuncture needles alone for 12 minutes followed by use of the low-level laser and the acupuncture needles together for 8 minutes.

In embodiments of the third aspect of the invention the preventive treatment sessions are carried out once every three months.

In embodiments of all aspects of the invention the treatment is carried out with the aid of at least one of:

a. personalized gloves that comprise holes directly over the specific acupoints that should be stimulated for the specific type of neoplastic process;
b. personalized socks that comprise holes directly over the specific acupoints that should be stimulated for the specific type of neoplastic process; and
c. an apparatus that is adapted to position and to support the stimulation means above the specific acupoint that should be stimulated for the specific type of neoplastic process at the correct location and angle.

In a fourth aspect the invention is a kit comprising instructions for diagnosing, preventing, and treating neoplastic processes by stimulation of specific acupoints. The kit may comprise at least one of:

a. stimulating means for carrying out the treatment; and
b. an apparatus for locating stimulating means on the specific acupoints.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

Figure 1:
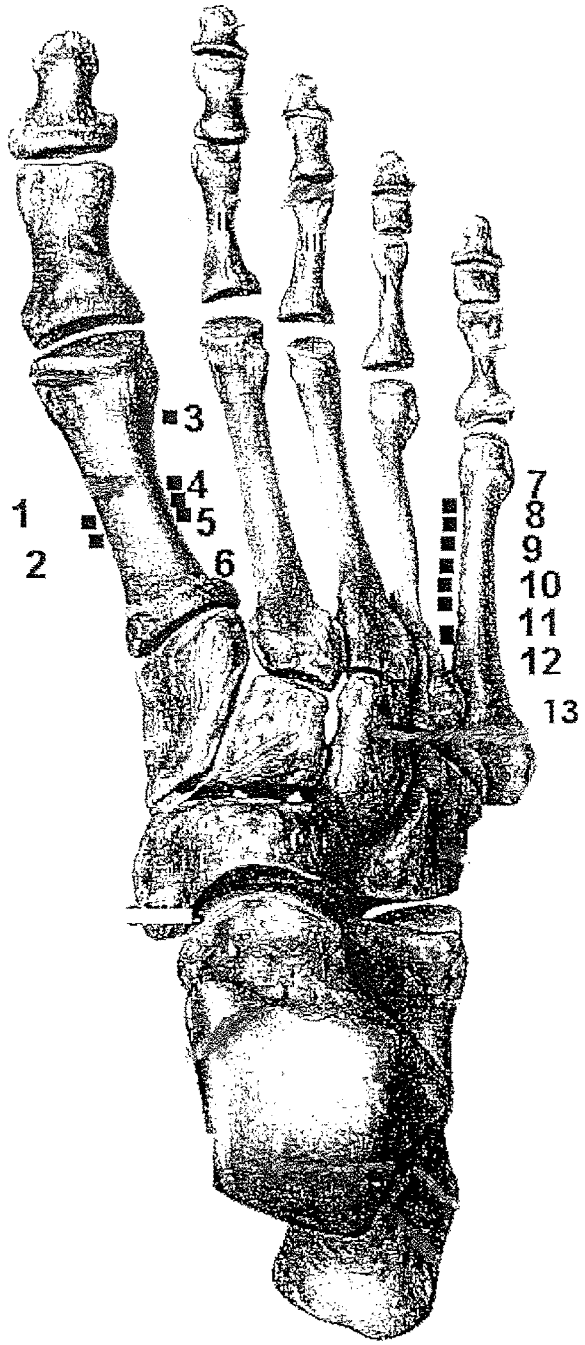
FIG. 1 and FIG. 2 respectively show the locations of the new acupuncture points of the invention on the bones of a right human foot and a right human hand.

The invention is a method consisting of stimulation of specific acupuncture points to prevent, detect, and treat specific types of neoplastic processes that occur in humans. Herein the term "neoplastic process" refers to the formation and growth of an abnormal growth of tissue in humans. The abnormal growth can be benign or malignant and is herein sometimes referred to as a cancer or a tumor. In many cases treatment according to the methods of the invention may lead to complete healing of the cancer.

The specific acupuncture points used in the method of the invention have not been previously disclosed as effective for the treatment of cancer. The treatments can be carried out by accredited practitioners in a clinical setting or by the patient her/himself or a layperson at home. When the treatments are carried out by the patient her/himself or a layperson at home, they can be guided by instructions from an accredited practitioner or by instructional material, e.g. instruction manuals, video recordings, and applications on mobile devices. The stimulation can be provided by any of the known techniques used for stimulation of controlling points, including traditional acupuncture needles, electric acupuncture, acupressure, laser, acupuncture laser, UV radiation, infra-red radiation, heat, fire, magnets, moxibustion, and a combination of two or more of these techniques, for example, the use of both needles and laser acupuncture simultaneously in a single treatment session or two lasers aimed at the same acupoint from different angles. In addition to the use of conventional acupuncture needles the inventors also envisage that an acupuncture needle supplied as an auto-injector similar to those used to inject insulin would be a very useful aid to many patients for self-treatments. Herein the generic term "stimulation techniques" refers to all of these techniques, but not limited to them, collectively. Herein the generic term "stimulation means" collectively refers to the devices or means, e.g. conventional needles, auto-injector needles, electric acupuncture apparatus, acupressure devices, lasers, UV radiation sources, infra-red radiation sources, heat sources, magnets, fire, and a combination of at least two of these means used to apply the stimulation techniques.

Equipment that can be useful in carrying out the method of the invention includes a laser device specifically designed for applying laser radiation to acupuncture points and apparatus including articles of clothing and an apparatus adapted to serve as guides to accurately locate the acupuncture points and apply the treatment.

The present invention differs from the earlier work described in the above referenced book authored by the first inventor in three ways: firstly new acupoints have been discovered for treatment of various types of cancer and secondly, in addition to acupuncture needles, other types of stimulation devices or combination of some of them are used to stimulate the acupoints and new acupuncture protocols have been developed. Thirdly, the method of the invention is adapted to be used for preventing, and/or detecting cancer—neither of which has been done using acupuncture techniques previously.

The first inventor has identified acupuncture points that are effective for stimulating the body for treatment of 16 different types of cancer in humans. The use of these acupuncture points in the treatment of cancer has never been reported before.

The types of cancer that can be treated using the new acupuncture points are: kidney, bladder, breast, stomach, pancreas, prostate, uterus, thyroid, small intestine, large intestine, ovary, rectal-anus, liver, testis, cervix, and lung.

Figure 2:
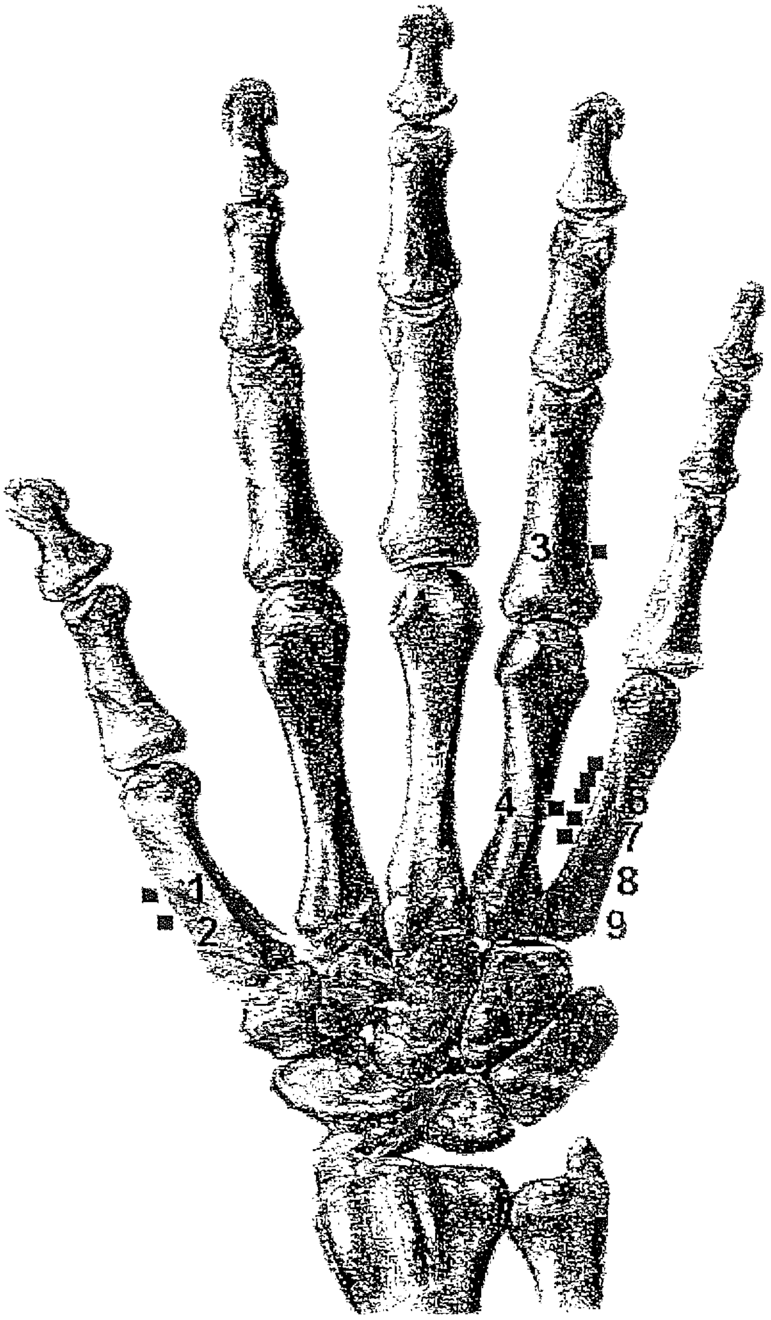

FIG. 1 and FIG. 2 respectively show the locations of the acupuncture points of the invention on the bones of a right human foot and a right human hand. In each of these figures a small black square represents the location of the acupoint and a number next to the square identifies the type of cancer that is treated by the respective acupuncture point. The acupoints numbered 1-13 in FIG. 1 will also be referred to herein as A1 to A13 respectively and the acupoints numbered 1-9 in FIG. 2 will also be referred to herein as B1 to B9 respectively.

All of the points are located close to the bones, as shown in the drawings. To indicate the locations of the points on the bones, the bone is divided into 20 parts, starting from the distal end (closest to the end of the finger or toe), and ending at the proximal end. The point is located then within a 1/20-part of the length of the bone, as listed in the following tables, wherein Table 1, relates to FIG. 1 and Table 2 to FIG. 2 and the first column in each table contains the numbers that identify the acupoints in the respective figure.

TABLE 1

Human Foot (FIG. 1)

| NUMBER | ORGAN | BONE | LOCATION |
|---|---|---|---|
| 1 = A1 | Kidney | Medial side of $1^{st}$ metatarsal | 10/20 |
| 2 = A2 | Bladder | Medial side of $1^{st}$ metatarsal | 11/20 |
| 3 = A3 | Breast | Lateral side of $1^{st}$ metatarsal | 6/20 |
| 4 = A4 | Stomach | Lateral side of $1^{st}$ metatarsal | 8/20 |
| 5 = A5 | Pancreas | Lateral side of $1^{st}$ metatarsal | 9/20 |
| 6 = A6 | Prostata & Uterus | Lateral side of $1^{st}$ metatarsal | 10/20 |
| 7 = A7 | Thyroid | Medial side of $5^{th}$ metatarsal | 4/20 |
| 8 = A8 | Small Intestine | Medial side of $5^{th}$ metatarsal | 8/20 |
| 9 = A9 | Uterus | Medial side of $5^{th}$ metatarsal | 10/20 |
| 10 = A10 | Ovary | Medial side of $5^{th}$ metatarsal | 10/20 |
| 11 = A11 | Prostate | Medial side of $5^{th}$ metatarsal | 11/20 |
| 12 = A12 | Large Intestine | Medial side of $5^{th}$ metatarsal | 12/20 |
| 13 = A13 | Rectum & Anus | Medial side of $5^{th}$ metatarsal | 14/20 |

TABLE 2

Human Hand (FIG. 2)

| NUMBER | ORGAN | BONE | LOCATION |
|---|---|---|---|
| 1 = B1 | Liver | Medial side of $1^{st}$ metacarpal | 10/20 |
| 2 = B2 | Testis | Medial side of $1^{st}$ metacarpal | 11/20 |
| 3 = B3 | Cervix | Lateral side of the proximal digital bone of the $4^{th}$ digit | between the distal 2/3 and the proximal 1/3 |
| 4 = B4 | Prostata & Uterus | Lateral side of $4^{th}$ metacarpal | 11/20 |
| 5 = B5 | Lungs | Medial side of $5^{th}$ metacarpal | 6/20 |
| 6 = B6 | Kidney | Medial side of $5^{th}$ metacarpal | 10/20 |
| 7 = B7 | Bladder | Medial side of $5^{th}$ metacarpal | 11/20 |
| 8 = B8 | Large Intestine | Medial side of $5^{th}$ metacarpal | 12/20 |
| 9 = B9 | Rectum & Anus | Medial side of $5^{th}$ metacarpal | 14/20 |

All of the acupoints shown in the figures and listed in Tables 1 and 2 have corresponding points on both hands or on both feet. For example, cancer of the liver in humans can be treated by stimulating acupoint 1 at the midpoint (10/20) of the medial side of the 1st metacarpal bone on the right hand as shown in FIG. 1 and an acupoint at the midpoint (10/20) on the medial side of the $1^{st}$ metacarpal bone on the left hand. In addition self-healing of some types of cancers, e.g. kidney, will be stimulated by stimulating acupoints on both the hand and the foot. In all of these cases the recommended treatment protocol calls for stimulating all of the points on both the left and the right sides, either simultaneously or consecutively.

According to the present invention, in addition to the use of needles, the accupoints can be stimulated by any known stimulation techniques. In particular the present invention proposes the use of low-level laser (also known as soft laser) radiation or a combination of needles and low-level laser radiation as will be described herein below.

Most devices used in laser acupuncture produce an output beam having a small footprint on the skin (typically a round footprint with a diameter of approximately 1 mm and an area of approximately 0.8 $mm^2$). One of the reasons that acupuncture treatments can only be administered by registered practitioners is the long learning curve need to learn how to locate the acupoints and accurately insert the needle. With needles the success of the treatment depends on accuracy of placement of the needles and the angle at which the needle is inserted, which in some cases is not perpendicular to the skin surface. With narrow output beam lasers similar conditions must be satisfied for successful treatment.

The inventors have conceived of the idea of using a laser apparatus that produces a long and narrow beam of laser light, which can be aligned with the bone and centered approximately at the location of the acupoint in order to overcome the problems associated with the level of exactness required when using needles or small diameter laser beams and to make it possible for non-professionals, including the patient her/himself, to administer the treatment following a recommended protocol. The laser device produces a fully coherent output beam (having an energy density that is uniform in magnitude over the entire rectangular, elliptical, or circular footprint, which in a non-limiting, illustrative embodiment can be approximately 450 $mm^2$. Using a laser device that produces an output beam having a large footprint on the skin that is powerful enough to stimulate the acupoint means that the center of the laser beam does not have to be located exactly over the acupoint.

The apparatus for producing the laser beam is similar to a commercially available apparatus that is manufactured and sold by the applicant of the present invention under the name B-CURE™ laser. This apparatus was designed and is being used to apply laser light for a wide variety of therapeutic purposes. The B-CURE™ laser is a light weight hand-held device that can be used by both health care professionals and non-professionals, including patients in their homes. The apparatus is described in patent applications that have been filed and published in several countries, e.g. US2011/0032960.

In order to see if the use of a large footprint laser beam as proposed in this invention could effectively produce similar results to those achieved using acupuncture needles a pilot investigation was carried out by the first inventor. The procedure consisted of stimulation of an area situated between Os metatarsale II and III in dogs having mammary cancer or mammary tumors. The stimulation of the area mentioned was done with direct and close laser radiation by a 250 mW B-CURE™ laser held against the area for 4 minutes, once a month for a total of 4 times.

The following table presents a summary of the results of treating mammary cancer in twenty dogs with a B-cure laser. The cases described represent a consecutive case series of treatment of dogs with mammary cancer. They were not selected to show, the best outcomes. The development of the tumors was followed up for several months.

TABLE 3

Summary of the Results of Treating Mammary Cancer with a "B-Cure Laser" soft Laser device

| # | Cancer type/description of tumour/malignancy and indication of malignant (M) or benign (B) | Patient/year of birth/Number of treatments | Results (positive effect (P), uncertain (?) or no effect (N)) |
|---|---|---|---|
| 1 | Mammacarcinoma/ 10 & 8 mm. tumors in both sides/(M) | Female dog, English setter/2009/3 | The tumors went almost totally away after 8 weeks, then reappeared 4 weeks later, and reached the size of ca 2-3 mm, and are now stable after 4 months. No other treatment (P) |
| 2 | Mammacarcinoma/ 65 mm. tumor left side/(M) | Female dog, Mastiff/ 2008/3 | The tumor did totally disappear after 6 weeks, and only a small lump of connective tissue of 3 mm remains. No other treatment (P) |
| 3 | Mammacarcinoma/6 tumors right side, differing between 3 and 11 mm/(M) | Female Dog, mixed breed/2006/3 | The tumors were totally gone after 11 weeks. No other treatment (P) |
| 4 | Mammacarcinoma/ 45 mm tumor left side/ (M) | Female dog, Riesenschnauser/ 2004/4 | The tumor shrank to 15 mm after 4 months. No other treatment (P) |
| 5 | Mammacarcinoma/ 94 mm tumor right side/(M) | Female dog, mixed breed/2009/3 | The tumor was reduced by 60% after 4 months. No other treatment. (P) |
| 6 | 1 Mammary tumour: diameter 1.1 cm/(B) | Female dog, English setter/2007/3 | The tumor is at the same size as when the treatment started 4 months ago. No other treatment. (?) |
| 7 | 2 Mammary tumours: diameter 14 mm and 11 mm right side/(B) | Female dog, English setter/2007/4 | The tumors are reduced by 15% after 4 months. No other treatment. (P?) |
| 8 | Mammacarcinoma/ 10 & 23 mm. tumors in both sides/(M) | Female dog, Riesenschnauser/ 2005/3 | The tumors continued to grow, but at a reduced rate. After 4 months the same results. No other treatment. (N) |

TABLE 3-continued

Summary of the Results of Treating Mammary Cancer with a "B-Cure Laser" soft Laser device

| # | Cancer type/description of tumour/malignancy and indication of malignant (M) or benign (B) | Patient/year of birth/Number of treatments | Results (positive effect (P), uncertain (?) or no effect (N)) |
|---|---|---|---|
| 9 | Mammacarcinoma/ 85 mm. tumor right side/(M) | Female dog, Golden retriever/2008/4 | The tumor is reduced with 80% after 3.5 months. No other treatment. (P) |
| 10 | 1 Mammary tumour: diameter 16 mm/(B) | Female dog, Mixed breed/2009/ | The tumor was reduced to 3 mm after 3.5 months. No other treatment. (P) |
| 11 | Mammacarcinoma/ 28 mm. tumors left side/(M) | Female dog, Buhund Norwegian/2006/3 | The tumor almost went totally away after 4 weeks, then reappeared 2 weeks later, and reached the size of ca 2-3 mm, and is now stable after 3 months. No other treatment (P) |
| 12 | Mammacarcinoma/ 55 mm. tumor left side/malign (M) | Female dog, Richback/2005/3 | The tumor totally disappeared after 6 weeks, and only a small lump of connective tissue of 3 mm remains. No other treatment (P) |
| 13 | Mammacarcinoma/4 tumors left side, 13, 18, 20 and 25 mm/ (M) | Female Dog, mixed breed/2006/3 | The tumors were totally gone after 10 weeks. No other treatment (P) |
| 14 | Mammacarcinoma/ 45 mm tumor left side/ (M) | Female dog, Grand Danois/2004/3 | The tumor has shrank to 15 mm after 3 months. No other treatment (P) |
| 15 | Mammacarcinoma/ 114 mm tumor left side/(M) | Female dog, mixed breed/2009/3 | The tumor was reduced to 34 mm after the 3 months. No other treatment. (P) |
| 16 | 1 Mammary tumour: diameter 30 mm right side/(B) | Female dog, Pekingnese/2005/3 | The tumor has grown to 35 mm in 3 months and 3 treatments. No other treatment. (?) |
| 17 | 3 Mammary tumours: diameter 14 mm and 21 mm and 34 mm, right side/(B) | Female dog, English setter/2008/3 | The tumors were reduced by 25% after 3 months. No other treatment. (P?) |
| 18 | Mammacarcinoma/ 30 & 43 mm. tumors in both sides/(M) | Female dog, Riesenschnauser/ 2006/3 | The tumors continued to grow for 2 months, but the last month there has been no growth. No other treatment. (N) |
| 19 | Mammacarcinoma/ 70 mm. tumor right side/(M) | Female dog, Golden retriever/2007/3 | The tumor is completely gone after 3 months. No other treatment. (P) |
| 20 | 1 Mammary tumour: diameter 15 mm/(B) | Female dog, Mixed breed/2009/3 | The tumor is reduced to 5 mm after 3 months. No other treatment. (P) |

The results here are similar to those that the first inventor has observed on >600 human and animal cancer patients in his own clinic using acupuncture needles to provide the stimulation to induce the self-healing. The overall results shown in table 3 are very promising. Of the 14 dogs with Mammacarsinoma there were 12 Positive results. Of the 6 dogs with Mammary Tumours there were 4 Positive results. In total 16 of the 20 dogs responded positively to the treatment. The positive effects were observed after 4 treatments over a total period of 4 months. These results provide a strong indication that stimulation of the specific acupoints using a large footprint laser beam will be effective also in the case of human cancers.

As mentioned above, one of the reasons that acupuncture treatments are carried out only by licensed practitioners is the level of experience necessary to accurately locate the acupuncture point and to insert the needle or align the laser beam. The inventors propose to overcome these problems by providing the following aids at least one of which can be employed by the user to assist him/her to accurately locate and stimulate the required acupoints:

A stimulation source in the form of a hand held device that illuminates a rectangular, elliptical, or round area of the skin of the patient with light. An embodiment of the light emitting stimulation source is a laser device that emits infrared radiation and comprises a second light source that emits a visible light that overlaps or outlines the invisible beam emitted by the infrared laser diode;

Personalized gloves (for acupoints on the hand) and socks (for acupoints on the foot), that comprise holes directly over the acupoints corresponding to the points that should be stimulated for the specific type of cancer.

An apparatus that is adapted to position and to support the stimulation means, e.g. laser device or needle, above the acupoint at the correct location and angle.

A video camera can be used to observe the relevant body part and produce images that, when used in conjunction with a processor and appropriate software and optionally with input from an experienced practitioner, can be displayed to the user to enable him/her to locate the desired acupoint and to insert the needle or aim the laser beam to that spot. In embodiments of the invention the user and the licensed acupuncturist or doctor are at separate locations. Both possess devices, e.g. smartphones, tablets, or computers, comprising dedicated software and connected to a communication network, e.g. the internet or a cellular network, which allows them to share images taken by the video camera and other information and to communicate with each other. In these embodiments the practitioner can be actively involved in the home treatment session, for example by marking the location of the acupoint/s to be treated on the screen image of the patient.

Figure 3:
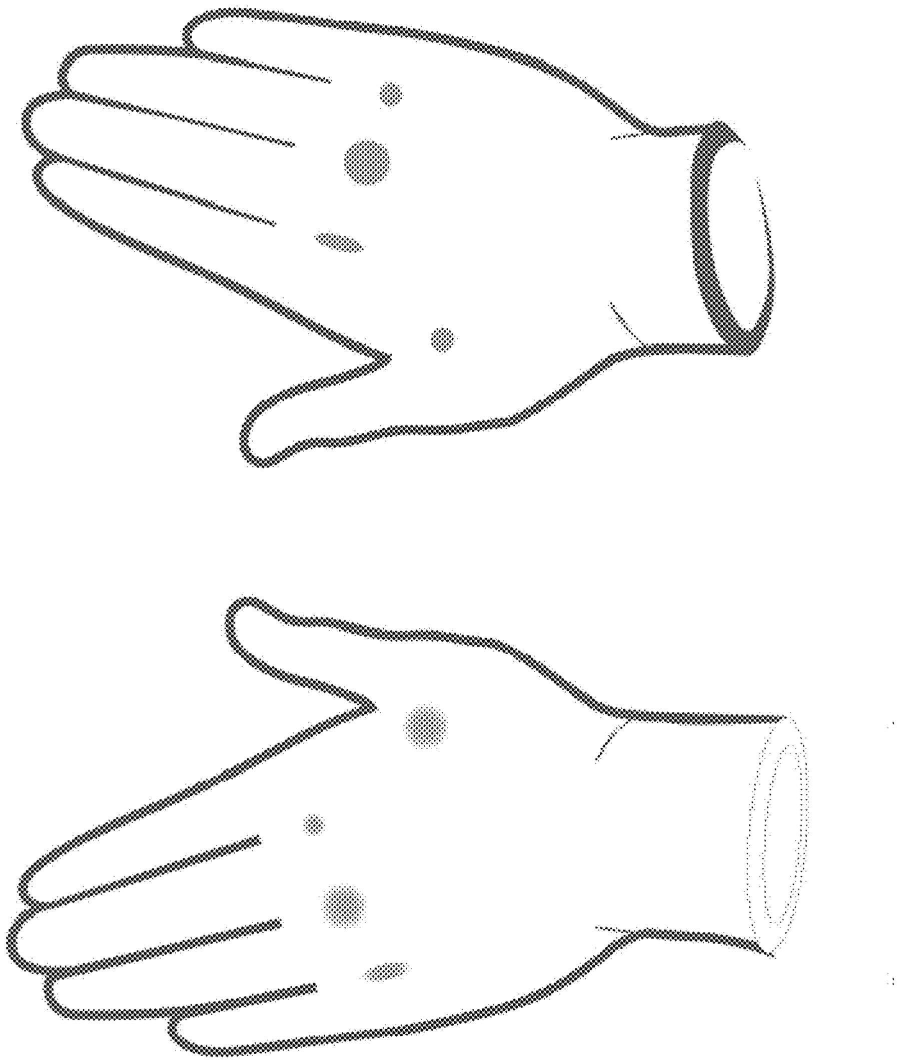
FIG. 3 schematically shows a glove adapted for use in the method of the invention.

FIG. 3 schematically shows a glove adapted for use in the method of the invention. The glove is provided in a number of sizes and in left and right hand versions to insure a correct fit to the hand of the patient.

Unpersonalized gloves can be produced in a number of models, each with pre-cut holes at the known location of the acupoints for treatment of one or more types of disease or conditions. Embodiments of the unpersonalized gloves will be made available with the size, and the name of the disease/s the holes represent printed on them.

The glove shown in FIG. 3, or at least part of it, can be made from transparent material, to assist in locating the acupoint. Socks can be adapted mutatis mutandis for use in applying the therapy in a manner similar to the glove.

Alternatively, the attending physician or accredited acupuncture practitioner that recommends and supervises the treatment can personalize the glove or sock by creating holes at the location of the acupoints that are appropriate for the specific symptoms of his patient. In order to individualize the glove or sock such that the placement of the holes conforms to the exact anatomical structure and dimensions of the patient, in embodiments of the gloves and socks at least a part of the glove or sock is manufactured from transparent material. In the first session with the practitioner, the patient puts on the glove or sock having the closest fit to her/his body and the practitioner locates the appropriate acupoint/s on the patient's body, marks the location/s on the glove or sock, and makes holes of the required size. In one embodiment the practitioner, guided by FIGS. 1 and 2, locates the acupoints and marks them on the skin before the patient puts on the article of clothing. The marks on the skin can then be seen through the transparent material and transferred to the article of clothing to mark the locations at which the holes should be created.

These holes in the glove or sock will allow the patient to apply the stimulation treatment by him/herself, whether using traditional acupuncture needles, auto-injector needles, a prior art narrow beam laser device, the wide beam laser device described herein above, a combination of needles and the wide beam laser device simultaneously, or any other stimulation means.

Embodiments of the gloves and socks comprise ridges around the holes or have a framework attached to them over the holes. The ridges or framework are adapted to help to hold the device used to apply the stimulation in a fixed position and orientation over the acupoint.

Figure 4:
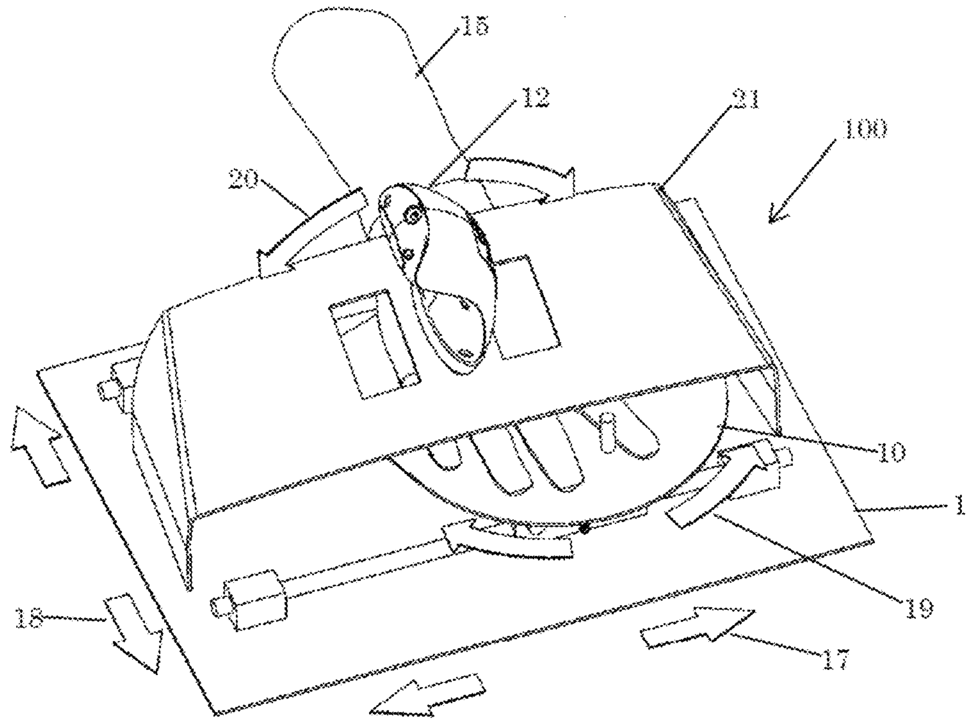
FIG. 4 to FIG. 6B schematically show an apparatus adapted to allow an inexperienced person to administer acupuncture treatment.
Figure 5:
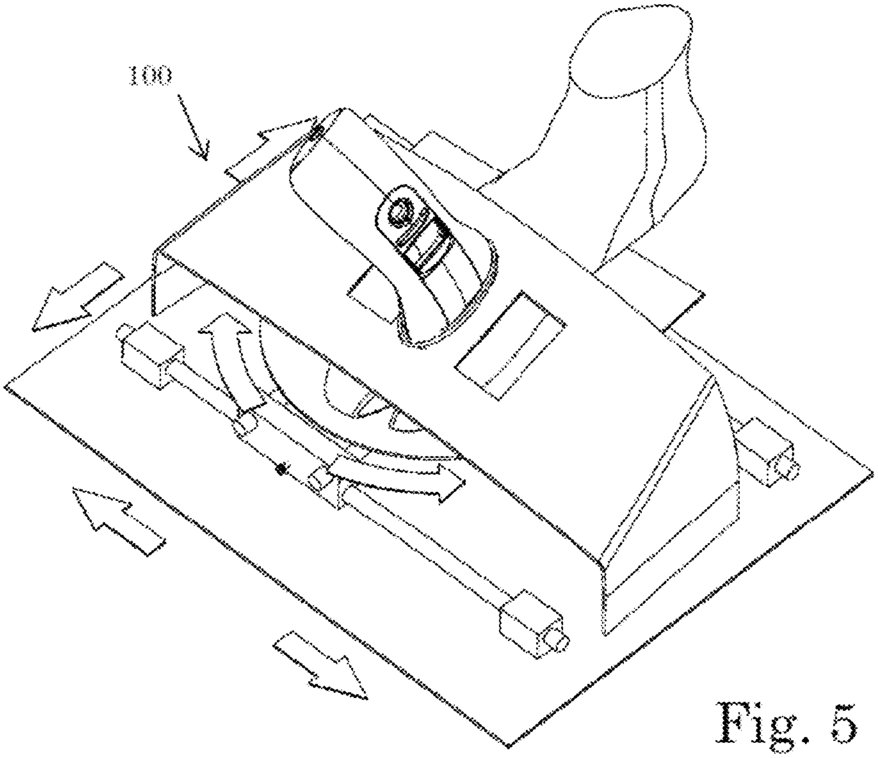

FIG. 4, FIG. 5, FIG. 6A, and FIG. 6B schematically show an apparatus adapted to allow an inexperienced person to administer acupuncture treatment. The apparatus is designed to position the stimulation device at the correct location over the acupoint and at the correct angle and to support the device during the treatment period. FIG. 4 shows the apparatus adapted for use with a hand. FIG. 5 shows the apparatus adapted for use with a foot. The main features of apparatus 100 are identified in FIG. 4. Other components of apparatus 100 are described in more detail with respect to FIG. 6A and FIG. 6B.

The framework of apparatus 100 that supports all other components is comprised of a base plate 1 to which is rigidly attached a rigid bridge 21. Between the base plate 1 and bridge 21 is located a platform 10. Platform 10 is mounted in such a way that it has two linear degrees of freedom—back and forth and right and left motion in directions parallel to two perpendicular sides of base plate 1 (indicated by arrows 17 and arrows 18) and one rotational degree of freedom—clockwise and counterclockwise (indicated by arrows 19) around an axis perpendicular to base plate 1 that passes through the center of platform 10. In the center of the bridge is at least one opening through which the laser device 12 is placed so that it can irradiate the surface of platform 10. A framework 13 which supports laser device 12 is attached to the bridge at the edge of the opening by means of a hinge adapted to allow laser device 12 to be tilted (indicated by arrows 20) relative to the surface of bridge 21. The tilt of the laser device gives the apparatus a fourth degree of freedom, which is important because some of the acupoints are located on the side of a bone and have to be stimulated at an angle to the perpendicular to achieve a positive result from the treatment. The organ 15 being treated is placed on the platform 10, which is moved until the location of the acupoint to be treated is under the center of the laser device 12. Platform 10 is now fixed in the correct position and at the correct orientation by locking its tilt angle and linear and rotational movements and the treatment can be started. In embodiments of the invention the locking mechanisms for the translational, rotational, and tilt motions comprise a series of marks that identifies the position at which each of the respective mechanisms is locked. After the initial location of the point at which the therapy should be applied is determined by the practitioner, the values of these marks are recorded and form a part of the treatment protocol for the patient, enabling the correct location for applying the therapy to be easily found in subsequent sessions.

Figure 6A:
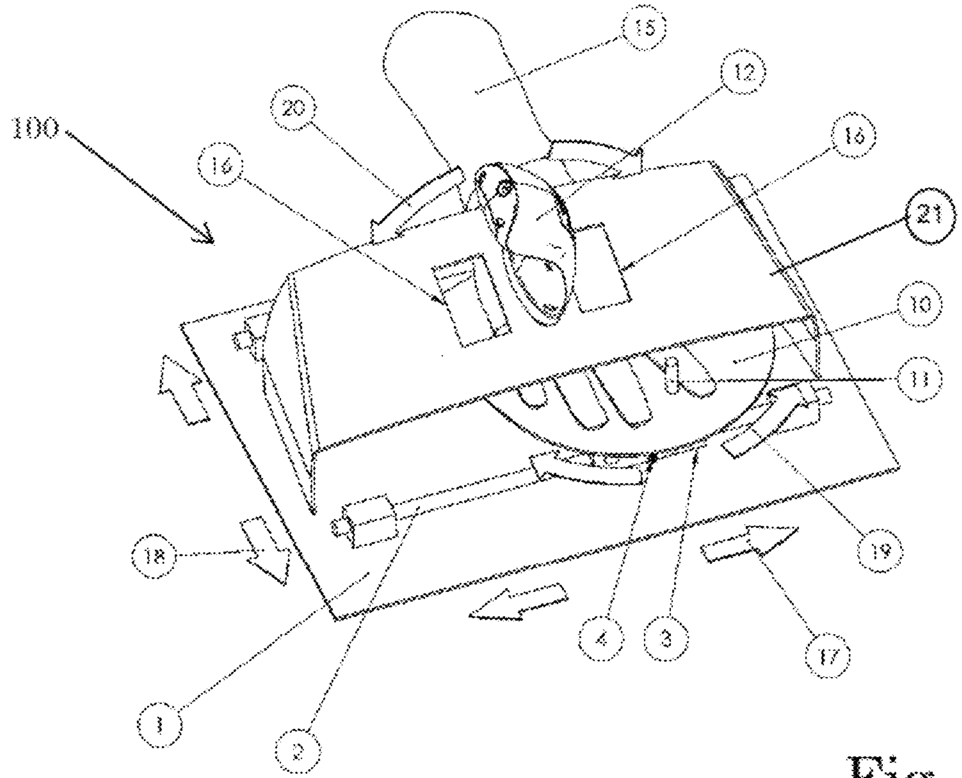
Figure 6B:
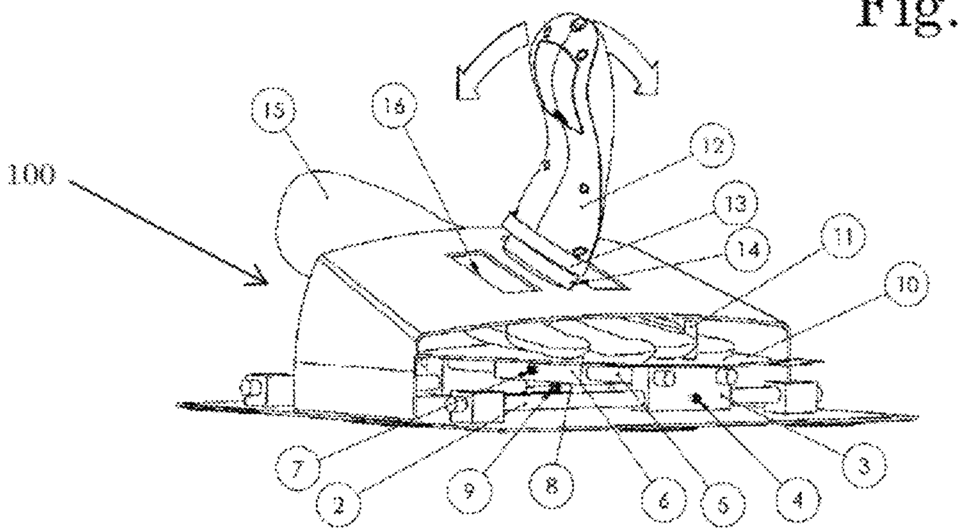

Referring to FIG. 6A and FIG. 6B other components of apparatus 100 are:

- X-direction rail 2, two parallel rails 2 are attached on opposite sides of base plate 1;
- X-direction carriage 3, one of which rides on each of rails 2;
- X-direction carriage lock 4, which, when locked, prevents movement of carriage 3 along rail 2;
- Y-direction rail 5, two parallel rails 5 are attached at their ends to the two carriages 3;
- Y-direction carriage 6, one of which rides on both of rails 5;
- Y-direction carriage lock 7, which, when locked, prevents movement of carriage 6 along rails 5;
- Z-axis pivot 8, which is attached to carriage 6 and supports platform 10;
- Z-axis lock 9, which, when locked, prevents rotation of platform 10;
- Locating pins 11, used to position the organ 15 to be treated, e.g. hand, on platform 10 and to maintain that position during the alignment and treatment procedures;
- Framework 13 of laser device 12;
- Hinge 14 that connects framework 13 to bridge 21 of apparatus 100 (not shown in the figures is a lock to prevent tilt of laser device 12); and
- Windows 16 or openings in the top of bridge 21 that allow observation of the treatment area on the organ 15 being treated.

In the figures the apparatus 100 is adapted for use with a wide beam laser device but apparatus 100 can be modified mutatis mutandis for use with any of the stimulation means that is used to apply acupuncture treatment, e.g. conventional acupuncture needles or other types of laser devices.

Because apparatus 100 supports the stimulation and healing device during treatment, it is especially useful in a clinical environment where the use of several of these apparatuses will allow a single practitioner to simultaneously treat several acupoints on the same patient, e.g. the corresponding point on the right and left hand, or to treat several patients simultaneously. The use of more than one apparatus will eliminate the advantage that the use of needles has over lasers in treatment protocols that require stimulation of several acupoints on the same patient to be treated at once.

In embodiments of the invention a glove (or sock) similar to that shown in FIG. 3 is used in conjunction with apparatus 100 in order to more easily locate the desired acupoint.

An embodiment of the method of the invention for treatment of a patient known to have a cancer affecting one of the organs listed herein above is carried out as follows:

The patient visits his attending physician, oncologist, or accredited acupuncture practitioner who identifies the acupoints to be stimulated and prepares a therapy protocol.

If the patient is taking medication for treatment of the disease, she/he is encouraged to continue with this during the course of the treatment according to the method of the invention.

Initially the treatment sessions will be carried out once a week for at least 3 months.

The duration of each treatment session depends on the type of stimulation that will be applied to the acupoints. Each treatment session with the laser apparatus will last for 8-10 minutes for each relevant acupoint. Treatment sessions using acupuncture needles will last 20 minutes per acupoint. For treatment sessions using a combination of needles and laser light, the needles only will be used for the first 12 minutes followed by stimulation with both the laser and the needles for 8 minutes.

The treatment sessions can be carried out by health care professionals in a hospital, clinic, or home environment; however, because of the relatively low cost and ease of operation of the laser apparatus, it is envisaged by the inventors that most of the sessions using the laser apparatus will be carried out by the patient or a family member or layperson in a non-clinical setting, e.g. the patient's home. Other scenarios are possible, e.g. one session per month carried out by an acupuncture practitioner followed by three home sessions with the laser apparatus or all self-treatments without the assistance of a professional. Where, and by whom, the stimulation will be administered will be determined on an individual basis taking into account factors such as the patient's ability to come to the clinic when required, the ability of the patient to carry out the sessions according to the schedule, and financial considerations.

The patient periodically visits his attending physician or oncologist who uses known methods to evaluate the effect of the treatment on the tumour.

According to the progress the physician, oncologist, care giver, or accredited acupuncture practitioner adjusts the treatment protocol, e.g. the type of stimulation to be applied and duration and frequency of treatment sessions.

This cycle is repeated as long as necessary until the treatment is deemed successful. As a general rule it is anticipated that in most cases positive results will be seen in three months, therefore it is recommended anyway not to stop the treatment before the end of the third month. After successful treatment it is recommended to continue with the treatment at a clinic or at home for a much longer period of time, for example once every month for the first year, and once every two months for life.

During acupuncture treatment sessions using either needles or laser devices some human patients report feeling sensations, which are usually described as a very moderate uneasiness and slight pain in the affected organ, and are interpreted to mean that something "is happening" in the relevant organ. Also the specific acupoint which refers to a specific kind of cancer is more sensitive to any form of stimulating means, including, but not limited to, a needle, a soft laser beam, or to a physical pressure. Having these sensations does not mean that the treatment will work better, but it is a good sign, which helps the patient to gain confidence in the treatment. In cases where good results are achieved, the patients feel the sensations with increasing lower intensity as the sessions progress and simultaneously the acupoints may become less sensitive. Observing these phenomena has led the inventors to the conclusion that stimulating the acupoints one at a time in any of the ways described above and receiving feedback from the patient can be used for early diagnosis of cancer in the organ associated with the specific acupoint. The diagnosis can then be confirmed or dismissed by other tests, e.g. mammography.

The acupoints taught by this invention can be used for self-diagnosis by any person but in particular by individuals at high risk of contracting a specific type of cancer. These persons should use any of the devices and methods taught herein to stimulate the acupoint relevant to the specific type of cancer once every three months. If they feel "sensations" in the organ in which the disease is located or at the acupoint then there is reason to believe that the cancer might be present and they should go immediately to be checked by a doctor. The absence of "sensations" does not mean that the disease is not present; however sensations at the stimulated acupoint that goes beyond those felt by at other stimulated acupoints or sensations in the organ that might be diseased after the diagnostic treatment certainly attest to the probability of developing the disease—therefore the importance of going to a doctor to be tested.

Furthermore, because using the laser acupuncture is easy to do at home, it is recommended that any person who wishes to do so and specifically individuals at high risk of contracting a specific type of cancer, as determined by family history or their genetic makeup, follow a protocol of laser radiation of the specific acupoint/s of this invention that is associated with that type of cancer as a preventive treatment. An example of a protocol of a preventive treatment is a session, as described herein above, once every three months.

It is noted that although the gloves, socks, and apparatus described herein above are useful aids to help both experienced professional practitioners and inexperienced persons to locate and stimulate the acupoints, their use is not a requirement of the method. The acupoints can also be stimulated by use of a hand-held wide-beam laser device or by the use of needles in the conventional way for diagnosis, prevention, and treatment of cancer.

Although embodiments of the invention have been described by way of illustration, it will be understood that the invention may be carried out with many variations, modifications, and adaptations, without exceeding the scope of the claims.

The invention claimed is:

1. A method for treating, by stimulation of specific acupoints, neoplastic processes that have previously been diagnosed in an organ in human patients who are or are not currently undergoing other treatment, said method comprising the steps of:

a) generating a therapy protocol wherein the specific acupoints to be stimulated that are relevant for treatment of neoplastic processes occurring in specific organs are the acupoints A1 to A13 and B1 to B9 on the feet and hands of said patients;

b) treating said patient in a series of treatment sessions comprised of stimulation of said specific acupoints, which are located on his/her hands and feet, wherein said stimulation can be provided by at least one of any stimulation means used to apply acupuncture therapy;

c) applying known methods to evaluate the effect of the treatment on the neoplastic process; and d) adjusting said therapy protocol according to said evaluation of the progress;

wherein the specific acupoints associated with the following organs are:

i) bladder—A2=11/20 on the medial side of 1st metatarsal and B7=11/20 on the medial side of 5th metacarpal;

ii) breast—A3=6/20 on the lateral side of 1st metatarsal;

iii) cervix—B3=between the distal ⅔ and the proximal ⅓ on the lateral side of the proximal digital bone of the 4th digit;

iv) kidney—A1=10/20 on the medial side of 1st metatarsal and B6=10/20 on the medial side of 5th metacarpal;

v) large intestine—A12=12/20 on the medial side of 5th metatarsal and B8=12/20 on the medial side of 5th metacarpal;

vi) liver—B1=10/20 on the medial side of 1st metacarpal;

vii) lungs—B5=6/20 on the medial side of 5th metacarpal;

viii) ovary—A10=10/20 on the medial side of 5th metatarsal;

ix) pancreas—A5=9/20 on the lateral side of 1st metatarsal;

x) prostata—A6=10/20 on the lateral side of 1st metatarsal and A11=11/20 on the medial side of 5th metatarsal and B4=11/20 on the lateral side of 4th metacarpal;

xi) rectum—A13=14/20 on the medial side of 5th metatarsal and B9=14/20 on the medial side of 5th metacarpal;

xii) small intestine—A8=8/20 on the medial side of 5th metatarsal;

xiii) stomach—A4=8/20 on the lateral side of 1st metatarsal;

xiv) testis—B2=11/20 on the medial side of 1st metacarpal;

xv) thyroid—A7=4/20 on the medial side of 5th metatarsal; and xvi) uterus—A6=10/20 on the lateral side of 1st metatarsal and A9=10/20 on the medial side of 5th metatarsal and B4=11/20 on the lateral side of 4th metacarpal;

wherein, said locations are expressed as the lengths of the bones, which are divided into twenty parts starting from the distal end and each of said acupoints is located within the indicated 20th part of said bone.

2. The method of claim 1, wherein:

i) in step (a) said patient consults instructional material available to her/him and decides which of the specific acupoints should be stimulated and prepares a therapy protocol accordingly, without the assistance of her/his attending medical specialist or an accredited acupuncture practitioner;

ii) in step (b) the treatment sessions are carried out by the patient or a family member or another layperson;

iii) in step (d) the patient her/himself adjusts the treatment protocol with or without the help of her/his attending medical specialist or an accredited acupuncture practitioner.

3. The method of claim 1, wherein the at least one stimulation means is selected from the group including, but not limited to: traditional acupuncture needles, auto-injector needles, electric acupuncture apparatus, acupressure devices, lasers, UV radiation sources, infra-red radiation sources, heat sources, magnets, fire, and a combination of at least two of these means.

4. The method of claim 1, wherein the treatment sessions are initially carried out once a week for at least 3 months.

5. The method of claim 1, wherein each treatment, session comprises one of the following: using low-level laser radiation alone for 8-10 minutes for each relevant acupoint; using acupuncture needles alone for 20 minutes per acupoint; and using a combined treatment with acupuncture needles and low-level laser radiation comprised of using said acupuncture needles alone for 12 minutes followed by use of said low-level laser and said acupuncture needles together for 8 minutes.

6. The method of claim 1, wherein the corresponding points on both hands or on both feet are stimulated either simultaneously or consecutively.

7. The method of claim 1, wherein treatment sessions are carried out periodically for the remainder of the patient's life.

8. The method of claim 1 wherein the treatment session is carried out with the aid of at least one of:

a) personalized gloves that comprise holes directly over the specific acupoints that should be stimulated for the specific type of neoplastic process;

b) personalized socks that comprise holes directly over the specific acupoints that should be stimulated for the specific type of neoplastic process; and c) an apparatus that is adapted to position and to support the stimulation means above the specific acupoint that should be stimulated for the specific type of neoplastic process at the correct location and angle.

9. A method for the diagnosis of the probability of the presence of or probability of development of neoplastic processes in a human patient, the diagnostic method comprising:

a) carrying out a diagnostic session comprised of successively stimulating at least one of the acupoints A1 to A13 and B1 to B9;

b) receiving feedback from said patient related to the strength of any sensation said patient feels when each of said acupoints is stimulated; and c) determining said probability based on said feedback received from said patient, wherein the higher the intensity of the sensation felt by said patient on stimulation of each of said acupoints the higher the probability of development of a neoplastic process in the organ associated with said acupoint;

wherein the specific acupoints associated with the following organs are:

i) bladder—A2=11/20 on the medial side of 1st metatarsal and B7=11/20 on the medial side of 5th metacarpal;

ii) breast—A3=6/20 on the lateral side of 1st metatarsal;

iii) cervix—B3=between the distal ⅔ and the proximal ⅓ on the lateral side of the proximal digital bone of the 4th digit;

iv) kidney—A1=10/20 on the medial side of 1st metatarsal and B6=10/20 on the medial side of 5th metacarpal;

v) large intestine—A12=12/20 on the medial side of 5th metatarsal and B8=12/20 on the medial side of 5th metacarpal;

vi) liver—B1=10/20 on the medial side of 1st metacarpal;

vii) lungs—B5=6/20 on the medial side of 5th metacarpal;

viii) ovary—A10=10/20 on the medial side of 5th metatarsal;

ix) pancreas—A5=9/20 on the lateral side of 1st metatarsal;

x) prostata—A6=10/20 on the lateral side of 1st metatarsal and A11=11/20 on the medial side of 5th metatarsal and B4=11/20 on the lateral side of 4th metacarpal;

xi) rectum—A13=14/20 on the medial side of 5th metatarsal and B9=14/20 on the medial side of 5th metacarpal;

xii) small intestine—A8=8/20 on the medial side of 5th metatarsal;

xiii) stomach—A4=8/20 on the lateral side of 1st metatarsal;

xiv) testis—B2=11/20 on the medial side of 1st metacarpal;

xv) thyroid—A7=4/20 on the medial side of 5th metatarsal; and xvi) uterus—A6=10/20 on the lateral side of 1st metatarsal and A9=10/20 on the medial side of 5th metatarsal and B4=11/20 on the lateral side of 4th metacarpal;

wherein, said locations are expressed as the lengths of the bones, which are divided into twenty parts starting from the distal end and each of said acupoints is located within the indicated 20th part of said bone.

10. The method of claim 9, wherein the diagnostic session comprises one of the following: using low-level laser radiation alone for 8-10 minutes for each relevant acupoint; using acupuncture needles alone for 20 minutes per acupoint; and using a combined treatment with acupuncture needles and low-level laser radiation comprised of using said acupuncture needles alone for 12 minutes followed by use of said low-level laser and said acupuncture needles together for 8 minutes.

11. The method of claim 9, wherein the diagnostic sessions are carried out once every three months.

12. The method of claim 9 wherein the diagnostic treatment session is carried out with the aid of at least one of:

a) personalized gloves that comprise holes directly over the specific acupoints that should be stimulated for the specific type of neoplastic process;

b) personalized socks that comprise holes directly over the specific acupoints that should be stimulated for the specific type of neoplastic process; and c) an apparatus that is adapted to position and to support a stimulation means above the specific acupoint that should be stimulated for the specific type of neoplastic process at the correct location and angle.

13. A method for preventing the development of a neoplastic process in an organ of a person before the disease has been detected by known diagnostic methods, including a person having a family history or genetic makeup that increases his/her risk of contracting said neoplastic process, said preventive method comprising periodically carrying out a preventive treatment session comprised of stimulation of the specific acupuncture points selected from the acupoints A1 to A13 and B1 to B9 that are relative to said specific type of neoplastic process;

wherein the specific acupoints associated with the following organs are:

i) bladder—A2=11/20 on the medial side of 1st metatarsal and B7=11/20 on the medial side of 5th metacarpal;

ii) breast—A3=6/20 on the lateral side of 1st metatarsal;

iii) cervix—B3=between the distal ⅔ and the proximal ⅓ on the lateral side of the proximal digital bone of the 4th digit;

iv) kidney—A1=10/20 on the medial side of 1st metatarsal and B6=10/20 on the medial side of 5th metacarpal;

v) large intestine—A12=12/20 on the medial side of 5th metatarsal and B8=12/20 on the medial side of 5th metacarpal;

vi) liver—B1=10/20 on the medial side of 1st metacarpal;

vii) lungs—B5=6/20 on the medial side of 5th metacarpal;

viii) ovary—A10=10/20 on the medial side of 5th metatarsal;

ix) pancreas—A5=9/20 on the lateral side of 1st metatarsal;

x) prostata—A6=10/20 on the lateral side of 1st metatarsal and A11=11/20 on the medial side of 5th metatarsal and B4=11/20 on the lateral side of 4th metacarpal;

xi) rectum—A13=14/20 on the medial side of 5th metatarsal and B9=14/20 on the medial side of 5th metacarpal;

xii) small intestine—A8=8/20 on the medial side of 5th metatarsal;

xiii) stomach—A4=8/20 on the lateral side of 1st metatarsal;

xiv) testis—B2=11/20 on the medial side of 1st metacarpal;

xv) thyroid—A7=4/20 on the medial side of 5th metatarsal; and xvi) uterus—A6=10/20 on the lateral side of 1st metatarsal and A9=10/20 on the medial side of 5th metatarsal and B4=11/20 on the lateral side of 4th metacarpal;

wherein, said locations are expressed as the lengths of the bones, which are divided into twenty parts starting from the distal end and each of said acupoints is located within the indicated 20th part of said bone.

14. The method of claim 13, wherein each preventive treatment session comprises one of the following: using low-level laser radiation alone for 8-10 minutes for each relevant acupoint; using acupuncture needles alone for 20 minutes per acupoint; and using a combined treatment with acupuncture needles and low-level laser radiation comprised of using said acupuncture needles alone for 12 minutes followed by use of said low-level laser and said acupuncture needles together for 8 minutes.

15. The method of claim 13, wherein the preventive treatment sessions are carried out once every three months.

16. The method of claim 13 wherein the preventive treatment session is carried out with the aid of at least one of:

a) personalized gloves that comprise holes directly over the specific acupoints that should be stimulated for the specific type of neoplastic process;

b) personalized socks that comprise holes directly over the specific acupoints that should be stimulated for the specific type of neoplastic process; and c) an apparatus that is adapted to position and to support a stimulation means above the specific acupoint that should be stimulated for the specific type of neoplastic process at the correct location and angle.

* * * * *